(12) United States Patent
Jackson et al.

(10) Patent No.: US 7,860,731 B2
(45) Date of Patent: Dec. 28, 2010

(54) MONITORING AND FEEDBACK WIRELESS MEDICAL SYSTEM AND METHOD

(75) Inventors: David Bryan Jackson, Chapel Hill, NC (US); Ralph Ellsworth Cook, Durham, NC (US); Stephen R. Cole, Durham, NC (US)

(73) Assignee: Confidant Hawaii, LLC, Honolulu, HI (US)

( * ) Notice: Subject to any disclaimer, the term of this patent is extended or adjusted under 35 U.S.C. 154(b) by 1080 days.

(21) Appl. No.: 11/312,156

(22) Filed: Dec. 20, 2005

(65) Prior Publication Data

US 2006/0212316 A1        Sep. 21, 2006

Related U.S. Application Data

(60) Provisional application No. 60/637,686, filed on Dec. 20, 2004.

(51) Int. Cl.
*A61B 5/00* (2006.01)
*G06F 19/00* (2006.01)

(52) U.S. Cl. ................................ 705/3; 705/2; 600/300

(58) Field of Classification Search .................... 705/2, 705/3; 600/300
See application file for complete search history.

(56) References Cited

U.S. PATENT DOCUMENTS

| | | | |
|---|---|---|---|
| 5,601,435 A | 2/1997 | Quy | |
| 5,704,366 A | 1/1998 | Tacklind et al. | |
| 5,899,855 A | 5/1999 | Brown | |
| 5,911,132 A * | 6/1999 | Sloane | 705/3 |
| 5,918,603 A | 7/1999 | Brown | |
| 5,997,476 A | 12/1999 | Brown | |
| 6,248,065 B1 | 6/2001 | Brown | |
| 6,368,273 B1 | 4/2002 | Brown | |
| 6,381,577 B1 | 4/2002 | Brown | |
| 6,565,509 B1 | 5/2003 | Say et al. | |
| 6,589,169 B1 | 7/2003 | Surwit et al. | |
| 6,602,191 B2 * | 8/2003 | Quy | 600/300 |
| 6,743,022 B1 | 6/2004 | Sarel | |
| 6,949,073 B2 | 9/2005 | Sarel | |
| 6,968,375 B1 | 11/2005 | Brown | |
| 7,031,745 B2 | 4/2006 | Shen | |
| 7,056,289 B2 | 6/2006 | Kasper et al. | |
| 7,088,233 B2 | 8/2006 | Menard | |
| 7,138,902 B2 | 11/2006 | Menard | |
| 7,156,809 B2 | 1/2007 | Quy | |
| 7,161,484 B2 | 1/2007 | Tsoulakis | |
| 7,223,236 B2 | 5/2007 | Brown | |
| 7,237,205 B2 | 6/2007 | Sarel | |
| 7,258,666 B2 | 8/2007 | Brown | |

FOREIGN PATENT DOCUMENTS

| | | |
|---|---|---|
| WO | 95/32480 | 11/1995 |
| WO | 97/28736 | 8/1997 |

(Continued)

*Primary Examiner*—Linh Michelle Le
(74) *Attorney, Agent, or Firm*—Ward and Smith, P.A.

(57) ABSTRACT

A system and method are provided for obtaining medical data from a user, analyzing it and providing a feedback message. Existing home medical devices are connected to a data translation device which transmits the data to a cellular phone. The cellular phone transmits the data to a server where it is analyzed and a feedback message is transmitted back to the phone.

24 Claims, 3 Drawing Sheets

FOREIGN PATENT DOCUMENTS

| | | |
|---|---|---|
| WO | 97/28737 | 8/1997 |
| WO | 98/24358 | 6/1998 |
| WO | 98/38909 | 9/1998 |
| WO | 99/04687 | 2/1999 |
| WO | 99/14882 | 3/1999 |
| WO | 99/41682 | 8/1999 |
| WO | 99/44494 | 9/1999 |
| WO | 99/46718 | 9/1999 |
| WO | 00/36900 | 6/2000 |
| WO | 00/40145 | 7/2000 |
| WO | 00/54205 | 9/2000 |
| WO | 00/62662 | 10/2000 |

* cited by examiner

MONITORING AND FEEDBACK WIRELESS MEDICAL SYSTEM AND METHOD

CROSS REFERENCE TO RELATED APPLICATIONS

This application is related to and claims priority to U.S. Provisional Application Ser. No. 60/637,686, and to the filing date thereof, which was filed Dec. 20, 2004 and is entitled Monitoring and Feedback Wireless Medical System and Method. The entire disclosure of Provisional Application Ser. No. 60/637,686 is hereby incorporated by reference herein.

FIELD OF THE INVENTION

This invention relates to a system and method for helping a patient manage his or her own medical condition by analyzing data obtained with at-home devices, transmitting the data for analysis and returning messages advising the patient. The invention also relates to a set of hardware components which can collect data from different types of devices and transmit data wirelessly to other systems for analysis and feedback.

BACKGROUND OF THE INVENTION

Medical personnel managing patients with chronic conditions like diabetes and Syndrome X with co-morbidities today have less and less time available to provide adequate monitoring and treatment. Attempts have been made to develop remote monitoring systems but they are generally complicated, require transmission over telephone lines, and require modem banks, service centers, and/or specific equipment for data collection. These systems do not provide adequate feedback to encourage and train patients to take better care of themselves.

Research has shown that effective communication between patients with chronic conditions and their clinicians is a key factor in developing a realistic, workable treatment plan. Further studies have shown that feedback provided to patients on a daily basis, though not automated, has created greater adherence to prescribed treatment regimens. A system providing automated feedback will lighten the workload for busy clinicians, lead to better outcomes for the daily management of chronic conditions, teach sustainable better healthcare habits, and empower the patient to feel in control of his or her treatment regimen.

A number of companies are currently involved in some form of remote patient monitoring for disease management. None provide direct, automated feedback based on remotely measured data, and thus do not provide for sustained improved behavior of the patient.

Studies have shown that addition of information systems in hospitals reduces liability and associated costs, and also that insurance costs for obese patients are higher than for normal weight patients. Historically, as is well known, life insurance premiums reflect documented health differences between smokers and non-smokers. Similarly, diabetics are likely to benefit from reduced weight if compliance with strictly prescribed regimens can be documented.

The problems with the prior art systems are avoided in accordance with the invention as described further herein.

BRIEF SUMMARY OF THE INVENTION

In accordance with one aspect of the invention, there has been developed an integrated system and method that creates sustainability of improved health outcomes and therefore decreased costs. The system provides a feedback loop that helps maintain improved behavior leading to improved health. The system relies on mobile phone technology and incorporates an analysis system on the back end.

In accordance with a more specific aspect, the invention relates to a system for monitoring a user's health and for modifying behavior related thereto. The system includes at least one medical device, such as a blood pressure monitor, blood glucose detector, etc., for detecting a specific user physical data. The medical device has connected thereto an interface device which is capable of transmitting the specific user physical data to a wireless cellular telephone, i.e., mobile telephone. The mobile phone is programmed to receive the specific user physical data and transmit the data to an analysis system having a database. The analysis system includes the database storing at least one type of user physical data, for example, blood pressure readings for a particular user, or blood glucose levels, which have been acquired over time for a specific user. The analysis system is programmed to analyze specific user physical data received from the wireless cellular telephone in relation to the previously acquired and stored data, and as a result of the analysis, a message can be transmitted to the wireless telephone concerning the user's medical circumstances resulting from the analysis conducted. The message can cause the user to modify behavior, for example, if blood glucose is too high, the user can receive an instruction to take remedial action. Another example is if blood pressure is too high, the user may be notified to start an exercise program, etc.

In an alternative aspect, there is provided a method for modifying a user's health and modifying behavior related thereto. The method involves detecting a specific user physical data with at least one medical device having connected thereto an interface capable of transmitting the specific user data to a wireless cellular telephone, i.e. a mobile phone. The user data is transmitted to the mobile telephone which is programmed for receiving the specific user physical data and for transmitting the data to an analysis system having a database. The data is transmitted to the analysis system which has stored therein at least one type of user physical data acquired over time for a specific user. The analysis system is programmed for analyzing the specific user data received in relation to previously acquired and stored user physical data. An analysis is conducted of the physical data received and a message is transmitted to the wireless cellular telephone concerning the user's medical circumstances, which resulted from the analysis conducted.

In accordance with another aspect of the system, a data translation device is employed which allows the use of existing home medical devices. More specifically, the data translation device transfers data to and from a home medical device over a serial port, for example, while performing any necessary buffering and data translation, and then acts as a slave device on a Bluetooth™ interface to transmit data wirelessly to another Bluetooth™ device such as a mobile phone.

The mobile phone, depending on the programming, can either immediately transmit the data wirelessly to the analysis system or store it for later transmission. At a central system, the data can be analyzed, along with medical parameters and historical measurement data, to determine current medical circumstances. The central system can then send messages to the user, and optionally to a guardian or clinician, for monitoring the medical condition and improving compliance with a recommended regimen. The messages are tailored to the various classifications of a user according to mental age, preferred language, and even cultural background. Preferably, the system operates in real time.

While described with reference to medical applications, it will be readily appreciated by those of ordinary skill in the art that the translation device can be used in a number of other applications, and preferably uses the standard "Bluetooth™" wireless communication protocol. The device is preferably powered by conventional batteries available to the general public and can have the wireless transmissions selectively enabled by a user.

In a yet still further aspect, the system of the invention is programmed to communicate with various devices using a data transmission hardware and software standard known as "RS232 Serial Interface". Other standards such as wireless, USB and IrDA can be implemented as an alternative to, or in conjunction with the serial interface. In accordance with the programming, communication with such devices is enabled without having to modify the program for new and different devices.

In a yet still further aspect, the invention is designed to read input data sent in regularly from a user's devices and return messages based on that data that help the user understand the data better. With reference to medical applications, it will be understood by those with ordinary skill in the art that such messages can help sufferers of chronic conditions manage those conditions better themselves, without requiring frequent intervention by medical professionals.

BRIEF DESCRIPTION OF THE SEVERAL VIEWS OF THE DRAWING

Having thus generally briefly described the invention, further additional details will be self-evident from the following detailed disclosure, made with reference to the appended drawings, wherein.

DETAILED DESCRIPTION OF THE INVENTION

Figure 1:
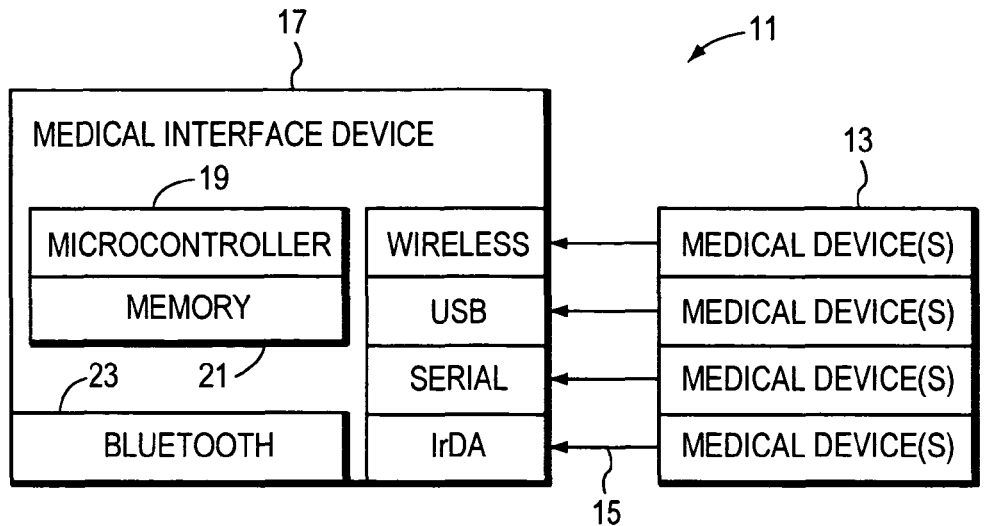
FIG. 1 is a block diagram illustrating medical devices connected to an interface device.

FIG. 1 illustrates a medical device/interface combination 11 as implemented in accordance with the invention. At least one medical device 13, or a plurality of medical devices can be connected through connections 15, through medical interface device 17. The connections can be through standard protocol such as wireless, USB, serial or IrDA.

Figure 2:
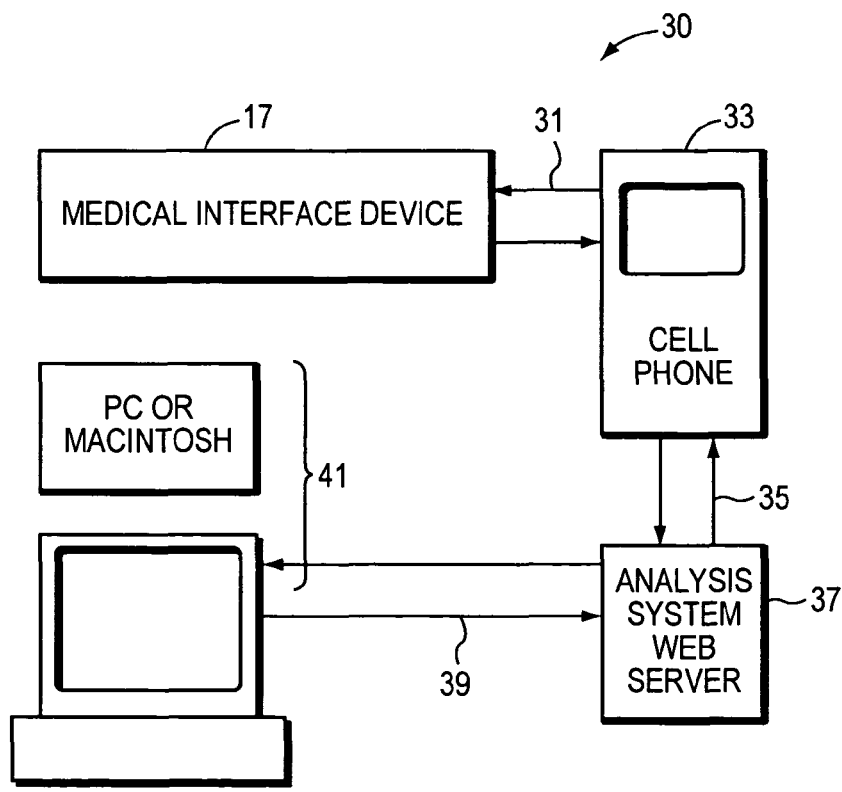
FIG. 2 is a block diagram illustrating the system of the invention.

The overall system 30 is shown in FIG. 2. The interface device 17 includes a microcontroller 19 with memory 21 and is programmed for receiving and processing information from the medical devices 13. A Bluetooth™ enabled functional module 23 serves to transmit medical or patient information acquired from a patient such as through a blood pressure monitor, glucose measuring device, and other associated devices including, for example, a weight scale, to a cellular phone 33 as illustrated in FIG. 2. The medical interface device 17 transmits the information 31 to the cellular phone 33 which is itself programmed for receiving the information, processing it and transmitting it through wireless message exchange 35 with an analysis system 37, for example, configured as a server 37 accessible through the internet. The server 37 is connected to a personal computer 41, through connections 39 to display the information to a clinician and process it in relation to previously acquired data about the patient. The clinician can then work with the system 37 from the computer 41 to, in accordance with preprogrammed protocols, transmit an appropriate message from the system 37 to the cellular phone 33. The message can involve a suggested change in protocol, such as change in diet because blood sugar is too high or the patient is overweight.

Figure 3:
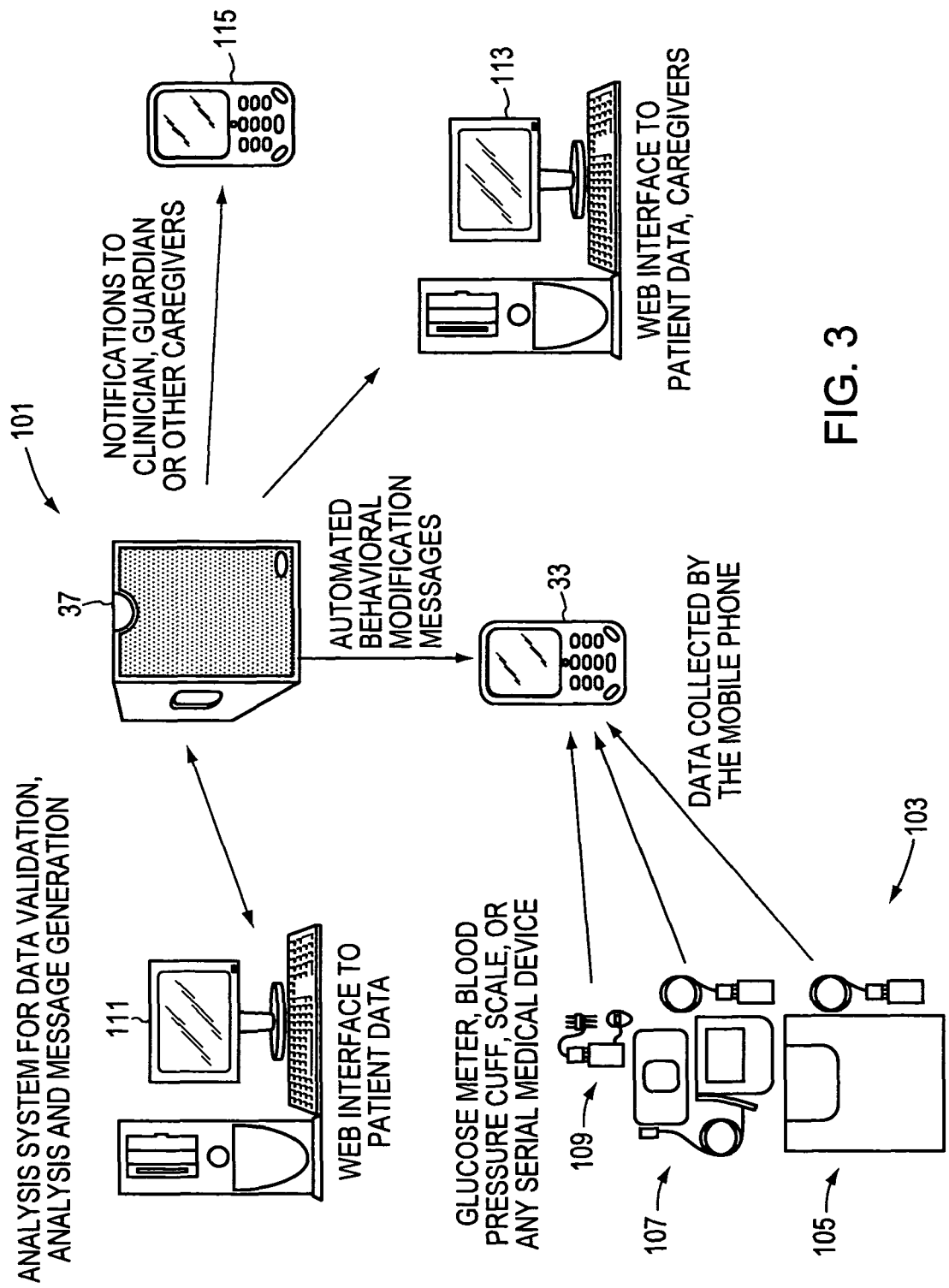
FIG. 3 is a diagram as in FIG. 2 illustrating the system of the invention in a more detailed embodiment with additional components.

As shown in the embodiment of FIG. 3, the additional embodiment 101 of the system of the invention can include more components. In this embodiment 101, the medical devices 103 with the medical interface device 17 (not shown) can be one or several of different types of devices such as a glucose meter 109, blood pressure cuff 107, scale 105, or any serial device. A web interface system 111 can be used to access patient data by a patient provided from analysis system 37. A web interface system 113 can also be implemented at a caregiver to allow access to patient data. Similarly, notification can be provided to a caregiver cell phone 115, programmed in a manner similar to the patient phone 33.

Figure 4:
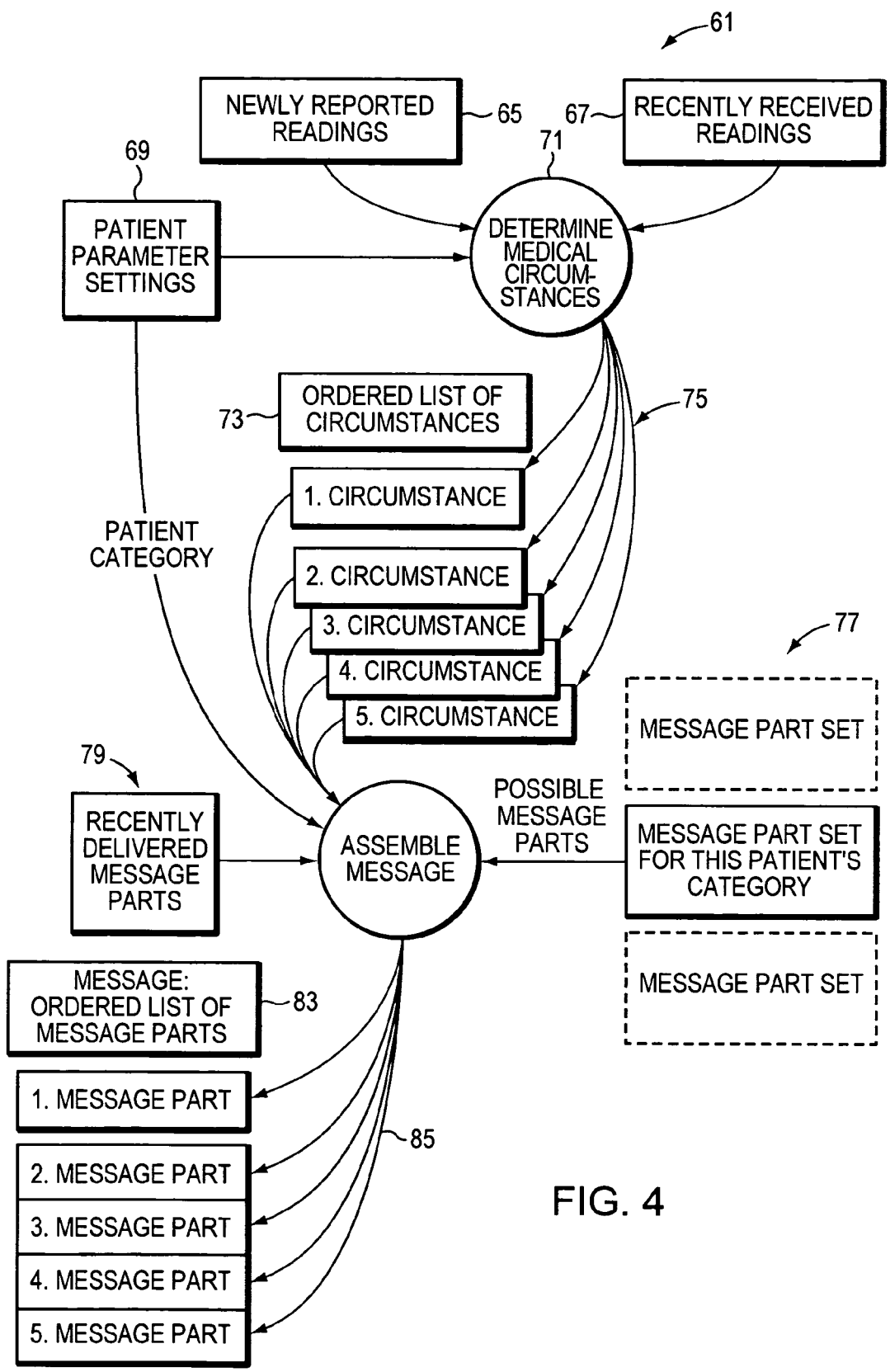
FIG. 4 is a flow diagram illustrating the method of the invention.

The method in accordance with the invention is illustrated in greater detail in the flow diagram of FIG. 4. More specifically, in order to properly fashion a message, newly reported readings 65 are received at the system 37 and assembled with recently received readings 67 for a particular patient. Patient parameter settings 69 are input and processed 71 to determine the medical circumstances for a particular patient. One or a plurality of outputs 75 result as an ordered list of circumstances 73.

The patient parameter settings are then combined with the circumstances, with a predetermined message set 77 and with recently delivered message parts to assemble a specific message 81 for the patient, either automatically, or through clinician interaction. The patient then receives an ordered list of message parts 83 which include at least one or a plurality of messages 85 which are transmitted to the cellular phone 33.

As may be appreciated, the system is an automated feedback loop for remote patient monitoring which includes the interface device 17 to communicate with off-the-shelf medical devices. It also includes, for example, a Bluetooth™ enabled cell phone 33 with a Java midlet, a server-based medical analysis system 37 which includes a data validation module and database, and a web client for both clinician and patient.

There are currently about 75 companies involved in some form of remote patient monitoring and/or disease management. The system of the invention 30 of FIGS. 2 and 3 is unique in (1) providing automated feedback immediately on being given new data, (2) providing feedback tailored to the type of patient, (3) requiring no personal computer, and (4) focusing on altering the behavior of and sustaining improved behavior of the patient. The system 30 of the invention allows providing service positioned to strengthen and support patient centered care. This patient-centered rather than clinician-centered view of treatment makes sense for lifestyle and health behavior that happens on a daily basis outside of the medical establishment. Research shows that effective communication between patients with chronic conditions and their clinicians is a key factor in developing a realistic and workable treatment plan that can be sustained over time as the majority of daily management of weight, diabetes, etc is carried out by the patient.

An additional advantage to the back-end analysis system 37 is the reduction of visits to the physician who is typically only reimbursed for face time with a patient and not for time spent on emails or phone calls. The analysis system 37 has the ability to recognize abnormal parameters and notify clinicians and patient guardians. This feature will assist the patient in bypassing unnecessary informational visits and will increase the timeliness of office visits when medically indicated.

The feedback loop as shown in FIG. 4 is critical to all product categories. Using off-the-shelf medical devices and customized feedback helps the sufferers of various chronic conditions manage their condition better. The analysis system 37 sends different kinds of messages upon gathering and analyzing data. First, it sends reminders and encouragement to the patient's cell phone 33 such as "need to make sure to take all glucose readings" or "you've been on target for two weeks, good work!" Second, it provides feedback to the health care organization through a web client. Clinical studies have demonstrated that active patient intervention through feedback leads to improved outcomes.

The system is unique in that it removes the personal computer at a patient site from the feedback loop, thereby gaining access to a larger target population. The system measures medically indicated data sets. More specifically, the analysis system 37 evaluates the information and provides feedback on behaviors. The advantages of the system are:

- The ability for the client to be mobile;
- Automated feedback as opposed to reliance on nurse or educator intervention;
- PC removed from loop making it simpler to use and available to non-computer literate patients;
- Monitoring patients becomes much more efficient and less costly while improving results; and
- It can be used as a "reminder" to reinforce compliance with desired behavior, i.e. taking medications, eating habits, monitoring vital signs.

Software on the analysis system 37 receives the data and runs it through an algorithm to decide what message(s) to send to the patient. This algorithm is based on (1) determining one or more medical circumstances from the data, and (2) choosing a message part based on the medical circumstances, the category of the patient, and recent messages sent to the patient. As will be readily apparent to those of ordinary skill, such an algorithm can be implemented in various ways given the parameters desired.

For purposes of the invention, a medical circumstance is a characterization of a medical state based on data sent in through the system and parameters set for the patient. The two areas currently examined for medical circumstance including the following:

(a) Has the patient has taken all prescribed readings for the day or week? The software determines whether the patient has "missed readings" to report, and calculates a score to help the patient understand how well he is doing maintaining his readings regimen. Examples of medical circumstance in this area are "Adherence score 95" and "missed N of M readings yesterday"

(b) Are reading values are within the ranges prescribed for the patient? The server calculates whether the patient has maintained his reading levels within the ranges specified by his doctor, and, if not, characterizes how far from his desired range he or she is. An example of a medical circumstance in this area is "blood glucose has been very high for the last week". The system defines possible circumstances for very low, low, high, very high, etc.

Other areas can be implemented for medical circumstance, for instance, trends in a reading can be analyzed for a circumstance of long-term changes in reading values, or combinations of readings can be examined for circumstances indicated by different readings together.

If the patient has more than one type of reading (such as blood pressure and blood glucose), the system determines medical circumstances for each area and for each reading type. Thus, when a patient reports a number of readings for a number of different reading types, the system determines a number of different medical circumstances based on those data.

The system defines an order for all possible circumstances based on what is most important for the patient to know. It puts all medical circumstances for one reported set of readings in decreasing priority order so that (1) message parts corresponding to the most important circumstances come first, and (2) the system can decide to deliver only a set number of message parts and be assured the most important message parts are being delivered.

Once all circumstances are determined, the system chooses a message part for each circumstance. First the system uses the patient's category to choose a set of message parts from which to pick. A patient category is chosen based on age, experience with the chronic condition, ethnic background, and/or psychological profile indicating what motivates this patient, or any other criteria chosen by his doctor to help him receive messages most likely to help him manage his condition.

Each set of message parts has one or more parts per possible medical circumstance and sequences of message parts for one circumstance are defined so that the patient does not see identical messages for a circumstance that continues, and so that stronger messages may be delivered for a circumstance that continues. Sequences of messages are delivered in a set order and the system determines whether the medical circumstance has been detected within a period of time (e.g., two weeks) and, if it has, determines which message in the sequence to use this time.

Sequences of messages can be rotating or linear. At the end of a rotating sequence, the system begins again at the first message in the sequence, and at the end of a linear sequence, the system repeats the last message.

The diagram of FIG. 4, previously discussed, summarizes the determination of medical circumstances and of the message that corresponds to them.

The patient cell phone 33 receives messages to help alter behavior. The patient is also able to go on a secure website hosted by the server 37 to view their data. The clinician has access to the automatically collected raw data, rather than relying on patient reports.

The system 30 lends itself to various configurations, which are outlines set forth in a non limiting manner, as follows.

1. Obesity Management.

U.S. National studies show that 60% of the 291 million Americans (roughly 175 million) are overweight and obese. The obesity iteration of the system's product line is desirable because people routinely pay out of pocket for products and services to help with this condition.

In an obesity implementation there is bundled as medical devices 13 an IrDA heart rate monitor, IrDA pedometer, serial digital precision scale, self-calibrating serial blood pressure cuff, and a interface device for each one. A Bluetooth™ enabled cell 33 phone is required from the patient (including a plan from their cell carrier). Importantly, the measurements include the miles walked per day, heart rate during the period, blood pressure at specific times, weight measurement, and the diet results for potential partners such as Jenny Craig™.

The gathered data are monitored against parameters set in the server and used to provide automatic feedback in the form of text on the patient's cell phone. A web server allows the patient to monitor the gathered data. There is also provided an internet chat room so a community of people with similar problems can chat with each other about what is working and what is not.

2. Diabetes Management.

It is estimated that approximately 177 million people in 130 countries, or about 5.2% in the age bracket 20-79, have diabetes. The South-East Asian Region has the highest number of people with diabetes with some 49 million, and its prevalence of 7.5% is the second highest, behind North America (7.8%), and ahead of the Eastern Mediterranean and Middle East Regions (6.4%).

By adding the ability to track Glucometer readings, the ability to provide feedback to the patient with Type 2 diabetes is gained. The Bluetooth™ cell phone is still preferred. People with Type 2 diabetes typically have been obese for some time and their bodies simply do not process insulin correctly. Intervention is not as aggressive, however, and since it is the largest market in diabetes, it is therefore critical to address. A 1996 NIDDK trial (DPP—Diabetes Prevention Program) involving over 3000 people showed that lifestyle intervention successfully reduced the development of diabetes in people age 60 and older by 71%.

Type 1 diabetes is an autoimmune disorder that requires active daily intervention to manage and it is also typically juvenile onset. The use of cell phones 33 in this patient group is viewed as an excellent communications tool. For this patient group a Continuous Glucose Monitoring (CGM) Device could be added as a medical device 13. The Bluetooth™ cell phone is still required. Tighter control of blood glucose is critical for people with Type 1 whose diabetes is difficult to manage with four isolated measurements per day. A 1% drop in HbAlc levels for a patient with diabetes represents a cost benefit per patient of $31,000; intensive feedback management has been shown to reduce HbAlc levels by 1.6% —these are the reductions in hospital utilization and overall health costs through proper management of diabetes, one component of syndrome X, that can be achieved through use of the technology supported case management feedback loop.

The benefit to the clinician is that the diabetic's logbook will be gathered and tracked automatically. Variation from plan by the patient is tracked by the analysis system and appropriate reminders will be sent to encourage compliance with the patient's prescribed regimen.

3. Cardiovascular Management

In the US, an estimated 12 million people have coronary heart disease, and risk factors including obesity, hypertension, and lack of exercise are increasing.

The cost of cardiovascular diseases and stroke in 2003 is estimated to be $351.8 billion, according to the American Heart Association and the National Heart, Lung, and Blood Institute (NHLBI). This figure includes both direct and indirect costs. Direct costs include the cost of physicians and other professionals, hospital and nursing home services, the cost of medications, home health care and other medical durables. Indirect costs include lost productivity that results from illness and death.

By adding the ability to track as medical devices 13 ECG/EKG data, Pulse Oximetry, and weight there is provided the ability to monitor the health of recent bypass patients and others at risk for cardiac episodes. The Bluetooth™ phone 33 is still required. Active monitoring is essential in the first few months of survival of a cardiac episode.

This system deals with more critically ill patients and system robustness must be guaranteed.

The system is convenient for the user:
Feedback messages arrive to cell phone. It is easier to carry than other internet devices;
Cell phone screens are easy to read;
No need for user to own a PC, since they can take system with them anywhere a cellular service exists; and
Using this system will add to patient confidence in achieving treatment goals.

Having this described the invention, the same will become better understood from the appended claims in which it is set forth in a non-limiting manner.

What is claimed is:

1. A system for monitoring a user's health and for modifying behavior related thereto, comprising:
at least one medical device for detecting a specific user physical data, said at least one medical device having connected thereto an interface device capable of transmitting said specific user physical data to a wireless cellular telephone;
at least one wireless cellular telephone programmed to receive said specific user physical data and to transmit said data to an analysis system having a database; and
an analysis system having a database storing at least one type of user physical data acquired over time for a specific user, said analysis system having a predetermined ordered list of a plurality of message parts and programmed to analyze specific user physical data received from said wireless cellular telephone, and in relation to previously acquired and stored user physical data, a medical circumstance of the user, a category of the user and recent messages sent to the user, as user parameter settings, for assembling a specific message for the user from said plurality of message parts based on one or more medical circumstances determined from the physical data received, category of user, recent messages sent to the user, and user parameter settings, either automatically or through clinician interaction, and for transmitting a message, assembled from specified message parts based on the medical circumstances determined, category of user, recent messages sent to the user, and user parameter settings to the wireless cellular telephone concerning the user's medical circumstances resulting from analysis conducted.

2. The system of claim 1, wherein said at least one medical device comprises a plurality of medical devices.

3. The system of claim 1, wherein said interface device and said wireless telephone are Bluetooth™ function enabled for conducting communication therebetween.

4. The system of claim 1, wherein said at least one medical device comprises an IrDA heart monitor, an IrDA pedometer, a serial digital precision scale and a self-calibrating serial blood pressure cuff for conducting obesity management, and each of said medical devices having its own interface device.

5. The system of claim 1, wherein said at least one medical device comprises a continuous glucose monitoring device for conducting diabetes management.

6. The system of claim 1, wherein said at least one medical device comprises an ECG/EKG monitor, a pulse oximetry monitor and a weight scale for conducting cardiovascular management.

7. The system of claim 1, wherein said analysis system comprises a server connected to a computer for allowing a clinician to review a user's data for creating a feedback message for the user.

8. The system of claim 7, wherein said server is also a web server which hosts a site allowing a user to securely view their data over the internet.

9. The system of claim 1, wherein said interface device comprises a wireless interface, a USB interface, a serial interface and an IrDA interface.

10. The system of claim 1, wherein said interface device includes a microcontroller and memory, and is programmed for transmitting data acquired to a cellular telephone.

11. The system of claim 1, wherein the analysis system is further programmed for transmitting the message to a third party cell phone.

12. The system of claim 1, wherein the message transmitted includes recommendations to cause the user to modify behaviors.

13. A method of monitoring a user's health and modifying behavior related thereto, comprising:
  detecting a specific user physical data with at least one medical device having connected thereto an interface capable of transmitting said specific user data to a wireless cellular telephone;
  transmitting said specific user data to a wireless cellular telephone programmed for receiving said specific user physical data and for transmitting said data to an analysis system having a database;
  transmitting said data to an analysis system having a database storing at least one type of user physical data acquired over time for a specific user and a predetermined ordered list of plurality of message parts, and programmed for analyzing the specific user physical data received from said wireless cellular telephone in relation to previously acquired and stored user physical data;
  conducting an analysis of the specific user physical data received, in relation to previously acquired and stored user physical data, a medical circumstance of the user, a category of the user and recent messages sent to the user, and user parameter settings;
  assembling a specific message for the user from said message parts based on one or more medical circumstances determined from physical data received, category of user, recent messages sent to the user, and said user parameter settings, either automatically or through clinician interaction, and
  transmitting the assembled message which is based on the medical circumstances determined, category of user, recent messages sent to the user, to the wireless cellular telephone.

14. The method of claim 13, wherein said data is acquired from a plurality of different medical devices.

15. The method of claim 13, wherein said transmitting of data to a wireless cellular telephone is conducted through a Bluetooth™ protocol.

16. The method of claim 13, wherein said at least one medical device comprises an IrDA heart monitor, an IrDA pedometer, a serial digital precision scale and a self-calibrating serial blood pressure cuff for conducting obesity management, and each medical device having its own interface device.

17. The method of claim 13, wherein said at least one medical device comprises a continuous glucose monitoring device for conducting diabetes management.

18. The method of claim 13, wherein said at least one medical device comprises an ECG/EKG monitor, a pulse oximetry monitor and a weight scale for conducting cardiovascular management.

19. The method of claim 13, wherein said analysis system comprises a server connected to a computer, and further comprising having a clinician review a user's data and delivering a feedback message to the user's wireless cellular telephone.

20. The method of claim 17, wherein said server is also a web server, and further comprising allowing a user to view his/her acquired data through a secure website.

21. The method of claim 13, wherein said interface device comprises a wireless interface, a USB interface, a serial interface and an IrDA interface.

22. The method of claim 13, wherein said interface device includes a microcontroller and memory, and is programmed for transmitting data acquired to a cellular telephone.

23. The method of claim 13, further comprising transmission the message to a third party cell phone.

24. The method of claim 13, wherein the message transmitted includes recommendations to cause the user to modify behavior.

* * * * *